(12) United States Patent
Song et al.

(10) Patent No.: US 12,121,628 B2
(45) Date of Patent: Oct. 22, 2024

(54) METHOD OF SURFACE TREATMENT OF TITANIUM IMPLANT MATERIAL USING CHLORIDE AND PULSE POWER AND TITANIUM IMPLANT PRODUCED BY THE SAME

(71) Applicant: INDUSTRY FOUNDATION OF CHONNAM NATIONAL UNIVERSITY, Gwangju (KR)

(72) Inventors: Ho Jun Song, Jeollanam-do (KR); Yeong Joon Park, Gwangju (KR); Hye Won Lee, Gwangju (KR); Moon Jin Hwang, Gwangju (KR); Hyun Joo Moon, Gwangju (KR); Woon Young Lee, Gwangju (KR)

(73) Assignee: INDUSTRY FOUNDATION OF CHONNAM NATIONAL UNIVERSITY, Gwangiu (KR)

( * ) Notice: Subject to any disclaimer, the term of this patent is extended or adjusted under 35 U.S.C. 154(b) by 460 days.

(21) Appl. No.: 16/713,168

(22) Filed: Dec. 13, 2019

(65) Prior Publication Data
US 2020/0188553 A1 Jun. 18, 2020

(30) Foreign Application Priority Data
Dec. 14, 2018 (KR) .......... 10-2018-0162342

(51) Int. Cl.
*A61L 27/06* (2006.01)
*B82Y 5/00* (2011.01)
*B82Y 40/00* (2011.01)

(52) U.S. Cl.
CPC .......... *A61L 27/06* (2013.01); *A61L 2400/18* (2013.01); *A61L 2420/02* (2013.01);
(Continued)

(58) Field of Classification Search
CPC .. A61L 27/06; A61L 2400/18; A61L 2420/02; A61L 2430/02; A61L 27/50;
(Continued)

(56) References Cited

U.S. PATENT DOCUMENTS 3,285,836 A * 11/1966 Maissel ............... H01L 21/00
205/213
3,410,766 A * 11/1968 Schmidt ................ C25D 11/26
361/524

(Continued)

FOREIGN PATENT DOCUMENTS

CN 102677126 A * 9/2012
JP 06154255 6/1994
(Continued)

OTHER PUBLICATIONS

Song et al. "Micro/Nano Hybrid Structured Surface Modification of Titanium Using Electrochemical/Hydrothermal Treatments" 2018 Spring Meeting of the KSBM, published Mar. 29, 2018 (3 pp).

(Continued)

*Primary Examiner* — Melanie R Tyson
*Assistant Examiner* — Melissa A Hoban
(74) *Attorney, Agent, or Firm* — Myers Bigel, P.A.

(57) ABSTRACT

The present disclosure provides a method for surface modification of a titanium implant material and a titanium implant obtained by the method for surface treatments. A titanium implant according to one embodiment of the present disclosure has high bond strength between implant and bone and its corrosion resistance.

6 Claims, 2 Drawing Sheets

(52) U.S. Cl.
CPC ............. *A61L 2430/02* (2013.01); *B82Y 5/00* (2013.01); *B82Y 40/00* (2013.01)

(58) Field of Classification Search
CPC ............. A61L 2400/12; A61L 2430/12; A61L 27/306; B82Y 5/00; B82Y 40/00; A61C 8/0015; A61C 13/0012; A61C 8/0006; A61C 13/02; A61C 2008/0046; C25D 11/024; C25D 11/026; C25D 11/26; A61F 2/30767

See application file for complete search history.

(56) References Cited

U.S. PATENT DOCUMENTS

| | | | | | |
|---|---|---|---|---|---|
| 3,700,569 | A | * | 10/1972 | Newby et al. | H01L 23/293 205/124 |
| 3,718,565 | A | * | 2/1973 | Pelletier | H01C 13/02 427/101 |
| 5,478,237 | A | * | 12/1995 | Ishizawa | A61C 8/0012 433/201.1 |
| 6,808,613 | B2 | * | 10/2004 | Beauvir | C25D 11/026 205/333 |
| 8,574,615 | B2 | * | 11/2013 | Tenney | A61P 41/00 424/423 |
| 2003/0108659 | A1 | | 6/2003 | Bales et al. | |
| 2012/0040254 | A1 | * | 2/2012 | Amendola | H01M 4/8615 977/734 |
| 2012/0118748 | A1 | * | 5/2012 | Jaworowski | B23K 35/36 205/108 |
| 2013/0001086 | A1 | * | 1/2013 | Yamashita | C25D 11/18 205/322 |
| 2017/0121841 | A1 | * | 5/2017 | Dolan | C25D 11/024 |
| 2018/0280143 | A1 | * | 10/2018 | Gorhe | C25D 11/26 |
| 2018/0280566 | A1 | * | 10/2018 | Kasinath | A61L 27/12 |
| 2018/0280571 | A1 | * | 10/2018 | Kasinath | A61L 27/32 |
| 2020/0078861 | A1 | * | 3/2020 | Sungail | B22F 1/052 |

FOREIGN PATENT DOCUMENTS

| | | | | |
|---|---|---|---|---|
| KR | 100910064 | B1 * | 7/2009 | ............. A61L 27/56 |
| KR | 101906258 | | 11/2012 | |
| KR | 1020120129270 | | 11/2012 | |
| KR | 1020160126513 | | 11/2016 | |
| TR | 201602690 | A * | 1/2017 | |

OTHER PUBLICATIONS

Park et al. "Fabrication of Micro/Nano Hybrid Porous Surfaces on Titanium And Their Surface Characterization" 9th International Nanomedicine Conference Jun. 25-17, 2018, published Jun. 25, 2018 (4 pp).

* cited by examiner

METHOD OF SURFACE TREATMENT OF TITANIUM IMPLANT MATERIAL USING CHLORIDE AND PULSE POWER AND TITANIUM IMPLANT PRODUCED BY THE SAME

BACKGROUND

1. Technical Field

The present specification claims the benefit of the filing date of Korean Patent Application No. 10-2018-0162342 filed with the Korea Intellectual Property Office on Dec. 14, 2018, the entire content of which is incorporated herein.

The present disclosure relates to a method for surface treatment of a titanium implant material and a surface-treated titanium implant obtained by the same, and more particularly, to a surface treatment method of imparting high roughness to increase the bonding strength of a titanium implant material with bone, and a surface-treated titanium implant obtained by the same method.

2. Related Art

Titanium has been most widely used as a dental implant metal because it has high biocompatibility and excellent corrosion resistance and mechanical properties. However, the titanium, a bioinert metal, shows slow bone formation in vivo, and hence various surface modification methods, such as a method of surface texturing or imparting chemical properties, or a method of coating the titanium metal with an osteoconductive material, have been used to enhance the bone-to-implant contact and osteoconductivity of a titanium metal.

One of representative methods for enhancing osteoconductivity is to impart appropriate roughness to the titanium metal surface. Methods that are most frequently used to this end include sand-blasted, large-grit, acid-etched (SLA) or resorbable blasting media (RBM) treatment, which strongly blasts the implant surface with sand or calcium phosphate-based compounds, acid etching treatment, plasma spraying treatment, and the like.

However, the method of increasing surface roughness by using the mechanical treatment has problems in that it is difficult to ensure the reproducibility of the roughness and metal surface is stressed by blasting materials. This method may also leave impurity particles on the titanium implant surface. In addition, the acid etching treatment has problems in that surface control is not easy and residues harmful to bone growth may also remain.

Accordingly, a method of modifying the surface of a titanium-based metal by electrochemical oxidation has recently attracted attention. When the titanium-based metal is adopted as an anode and treated using microarc oxidation method, a titanium oxide layer is formed on the surface of the metal, and this oxide layer may have the porous surface with micro and submicro sized-pores, thus increasing the osteoconductivity of the metal. Microarc oxidation is a method in which sparks are induced on the oxide surface layer by application of a high voltage during anodic oxidation of a metal in an electrolyte solution. The oxide layer is locally melted due to a high temperature generated at this time, and micro or submicro-sized pores are formed on the oxide layer surface.

The surface roughness value of titanium implant after these kinds of electrochemical treatments is about 0.4 μm. However, the surface roughness value obtained in the case of SLA or RBM treatment which is currently most frequently used as a method for surface treatment of a titanium implant is about 1 to 2 μm. Until now, it is very difficult for the conventional electrochemical method to provide a suitable roughness required for a titanium implant.

SUMMARY

An object of the present disclosure is to provide a method of surface-treating a titanium implant material by electrochemical treatment to have high surface roughness, and a surface-treated titanium implant obtained by the same method.

However, problems to be solved by the present disclosure are not limited to the above-mentioned problem, and other problems which are not mentioned will be clearly understood by those skilled in the art from the following description.

In accordance with one aspect of the present disclosure, there is a method provided for surface treatment of a titanium implant material, the method including: anodically oxidizing the titanium implant material in a chloride electrolyte solution by application of electrical pulses, to form a microstructured-surface of the titanium implant material and a titanium oxide layer on the titanium implant material; acid-etching the titanium implant material having the microstructured-surface and the titanium oxide layer thereon, to remove the titanium oxide layer; and performing microarc oxidation on the titanium implant material from which the titanium oxide layer has been removed, to form a titanium oxide layer again on the microstructured-surface of the titanium implant material.

In accordance with another aspect of the present disclosure, there is a titanium implant whose surface has a roughness of 2 to 3.5 μm with a hybrid structure, wherein the hybrid structure has microstructures on which nano-structured titanium oxide layer is formed.

DETAILED DESCRIPTION

Throughout the present specification, it is to be understood that when any part is referred to as "including" any component, it does not exclude other components, but may further include other components, unless otherwise specified.

Throughout the present specification, when any member is referred to as being "on" another member, it refers to not only a case where any member is in contact with another member, but also a case where a third member exists between the two members.

Throughout the present specification, the term "microstructure" may refer to a structure of a surface having roughness in micrometer units.

Throughout the present specification, the term "surface treatment" may refer to changing the surface structure of the outer surface of any component by a method such as an acidic or basic reagent treatment, an electrochemical oxidation treatment or hydrothermal treatment, etc.

Throughout the present specification, the term "hybrid structure" may refer to a surface structure of any component, and specifically, may refer to a structure including a microstructure and a nanostructured film or layer formed on the microstructure.

Hereinafter, the present disclosure will be described in more detail with reference to the accompanying drawings.

A method for surface treatment of a titanium implant material according to one embodiment of the present disclosure includes:

anodically oxidizing the titanium implant material in a chloride electrolyte solution by application of electrical pulses, to form a microstructured-surface of the titanium implant material and a titanium oxide layer on the titanium implant material;

acid-etching the titanium implant material having the microstructured-surface and the titanium oxide layer thereon, to remove the titanium oxide layer on titanium implant material; and performing microarc oxidation on the titanium implant material from which the titanium oxide layer has been removed, to form a titanium oxide layer again on the microstructured-surface of the titanium implant material.

In the present specification, the titanium implant material may refer to an implant material comprising a pure titanium metal or titanium alloys.

Figure 1:
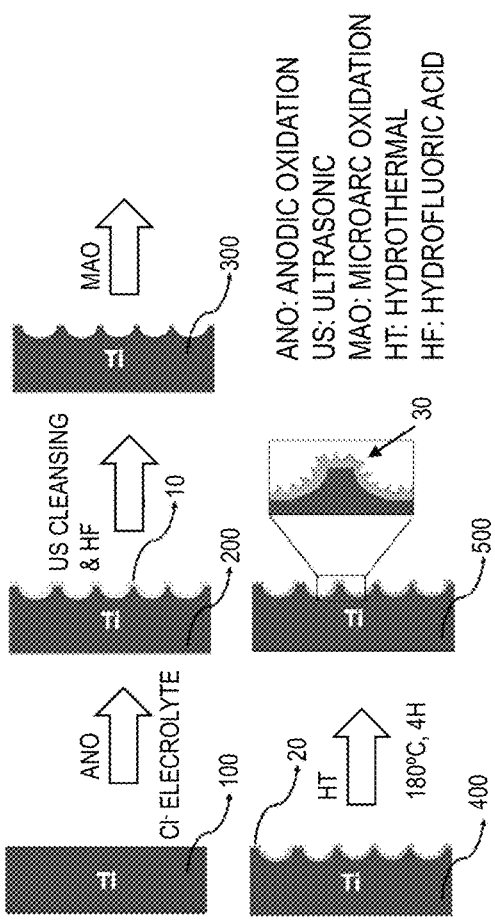
FIG. 1 is a schematic view illustrating each step of a method for surface treatment of a titanium implant material according to one embodiment of the present disclosure.

FIG. 1 is a schematic view illustrating each step of a method for surface treatment of a titanium implant material according to one embodiment of the present disclosure.

Referring to FIG. 1, first, a titanium implant material 100 is anodically oxidized in a chloride electrolyte solution (not shown) by application of electrical pulses, to form a microstructured-surface of the titanium implant material 200 and a titanium oxide layer 10 on the titanium implant material 200. Specifically, the chlorine ion contained in the chloride electrolyte solution reacts with titanium, and at the same time, the titanium on the surface thereof is oxidized, whereby a titanium tetrachloride compound may be formed with titanium oxide, and a titanium oxide layer 10 is formed on the surface of the titanium implant material 200. The formed titanium tetrachloride compound is a water-soluble material which is dissolved in the electrolyte solution.

According to one embodiment of the present disclosure, the anodic oxidation is performed by applying electrical pulses. During anodic oxidation, a large amount of bubbles are generated. However, in a direct-current anodic oxidation method using a constant current, it is difficult to effectively remove these bubbles. For this reason, by applying electrical pulses (voltage application), large amount of bubbles generated while the anodic oxidation process may be effectively removed during a time period in which the electrical signal is interrupted (rest period).

According to one embodiment of the present disclosure, the electrical pulses with a current density of 0.5 $A/cm^2$ to 3 $A/cm^2$ may be applied to the titanium implant. When a titanium alloy is treated, the treatment is preferably performed by applying electrical pulses with an increased current density, compared to the treatment of pure titanium. Specifically, when a pure titanium metal is treated, it is preferably anodically oxidized by applying electrical pulses with a current density of 0.5 $A/cm^2$ to 1.5 $A/cm^2$. More preferably, it is anodically oxidized by applying electrical pulses with a current density of 0.5 $A/cm^2$ to 1 $A/cm^2$. A titanium-based alloy is preferably anodically oxidized by applying electrical pulses with a current density which is generally about 1.5 to 2-fold higher than that for anodic oxidation of the pure titanium metal.

The application of the electrical pulse may be performed for a plurality of cycles, each consisting of current application for 1 second and rest for 4 seconds. That is, the electrical pulses may be applied at a frequency of 0.2 Hz. When a titanium alloy is treated, the treatment is preferably performed for an increased number of cycles, compared to the treatment of a pure titanium metal. That is, when the pure titanium metal is treated, the treatment is preferably performed for 50 to 100 cycles within the above-described current density range, and when the titanium alloy is treated, the treatment may preferably be performed for 100 to 150 cycles within the above-described current density range.

If the current density of pulses is too low, anodic oxidation will not be sufficient, which makes difficult to provide a uniform roughness to the surface, and if the current density of pulses is excessively high, there will be a risk of deformation of specimen shape due to excessive anodic oxidation. For this reason, the anodic oxidation is preferably performed within the above-described current density range.

According to one embodiment of the present disclosure, the titanium implant material is anodically oxidized in the chloride electrolyte solution. In this case, the titanium may be ionized and may react with the chlorine ion to produce titanium tetrachloride which is dissolved in chloride electrolyte solution, and the microstructures having a concave surface shape may be simultaneously formed on the surface of the titanium implant material, thus imparting high roughness. When the surface of the titanium implant material has high roughness, the titanium implant material may have increased osteoconductivity. Thus, when the titanium implant material is implanted in vivo, the bond strength of the implant with bone may increase and the time for which the implant is stably fixed on the bone may be shortened. That is, the implant treatment period may be more shortened.

According to one embodiment of the present disclosure, the chloride electrolyte solution may be a chloride electrolyte solution containing chlorine ions, and may preferably be an aqueous chloride solution. The chloride electrolyte is preferably a metal chloride electrolyte, and is particularly preferably $CaCl_2$ and NaCl. In addition, a simulated body fluid (SBF) also contains chlorine ions and is harmless to the human body, and thus may preferably be used as an electrolyte solution in the anodic oxidation step of the present disclosure.

According to one embodiment of the present disclosure, the chloride electrolyte solution may have a chlorine ion concentration of 0.2 M to 1.0 M.

When an electrolyte solution having a chlorine ion concentration within the above range is used, an appropriate anodic oxidation reaction occurs, and an oxide layer is formed on the surface by loose bonding, and thus is easy to remove. However, at a concentration lower or higher than the above-described chlorine ion concentration, an anodic oxidation reaction will not easily occur or uniformity will decrease.

Then, the titanium oxide layer formed on titanium implant material is removed by acid-etching treatment. Since the titanium oxide layer 10 formed together with the production of titanium tetrachloride is loosely bonded to the titanium implant material, it is easily removed by acid etching treatment, to obtain a titanium implant material 300 having the microstructured-surface.

According to one embodiment of the present disclosure, the acid etching treatment may be performed using a strong acid. In addition, the acid treatment may be performed using nitric acid or hydrofluoric acid (HF), preferably hydrofluoric acid.

According to one embodiment of the present disclosure, the method may further include a step of ultrasonically cleaning the titanium implant material with distilled water, before and after acid-etching the titanium implant material having the microstructured-surface and the titanium oxide layer thereon. When the titanium implant material is ultrasonically cleaned with distilled water, the ultrasonic cleaning corresponds to physical cleaning, and thus can remove titanium tetrachloride, titanium oxide layer, strong acid and other electrolyte agents, which have been attached to the surface of the titanium implant material.

Thereafter, the titanium implant material, from which the titanium oxide layer has been removed and which has the microstructured-surface, is treated by microarc oxidation, to form a titanium oxide layer again on the microstructured-surface of the titanium implant material. That is, the titanium implant material 300, from which the titanium oxide layer 10 has been removed, is treated by microarc oxidation, to form a titanium oxide layer 20 again.

A titanium oxide layer is spontaneously formed on titanium metal in the air, but the spontaneously formed titanium oxide layer does not produce a micro-rough surface needed for rapid osteoconduction. Accordingly, a titanium oxide layer needs to be artificially formed on the titanium implant material by specific treatment in order to increase the osseointegration of the implant material, enhance the safety of the implant material after placement in vivo, and impart corrosion resistance to the implant material. Using microarc oxidation, a titanium oxide layer may be formed again on the microstructured-surface of the titanium implant material.

According to one embodiment of the present disclosure, the microarc oxidation may be performed by applying a direct electric current power with 0.025 A/cm$^2$ to 0.03 A/cm$^2$ for 90 seconds to 180 seconds. Unlike the anodic oxidation mentioned above, a low current is applied.

According to one embodiment of the present disclosure, the microarc oxidation may be performed in an electrolyte solution containing a 0.1 M to 0.2 M calcium acetate monohydrate (CA) and 0.01 M to 0.02 M β-glycerophosphoric acid disodium salt pentahydrate (β-GP) electrolyte. When the microarc oxidation is performed in the electrolyte solution, a titanium oxide layer incorporated with calcium and phosphorus may be formed. When a calcium and phosphorus-containing titanium oxide layer is formed on the titanium implant, the bond strength of the titanium implant with bone may increase.

According to one embodiment of the present disclosure, the method may further include, after the step of forming the titanium oxide layer again on the microstructured-surface of the titanium implant material, a step of treating the titanium implant material to hydrothermal treatment. Through the hydrothermal treatment, titanium dioxide nanostructures 30 may be formed on the surface of the titanium oxide layer 20, to impart hybrid roughness structures to the surface of the titanium implant.

Hydrothermal treatment (HT) refers to treating a target materials with a high-temperature aqueous solution at high pressure. By hydrothermal treatment, the amorphous titanium dioxide formed on the surface may be transformed into the crystalized titanium dioxide having an anatase structure, and the nanostructured-surface may be formed. In addition, the hydrophilicity of the oxide layer may be increased, which means that the wettability of the oxide layer with body fluids and blood may be increased. Accordingly, the osseointegration process of the titanium implant after implantation may proceed successfully and the titanium implant may be stabilized quickly. In addition, the titanium oxide layer may be more stabilized, and thus may ensure corrosion resistance.

According to one embodiment of the present disclosure, the hydrothermal treatment may be performed in a NaOH alkaline solution. The pH of the solution may be about 11. When the pH value is about 11, nanostructures having an appropriate size may be formed on the titanium oxide layer, to increase the osteoconductivity of the titanium implant.

As the alkaline solution, an aqueous solution containing a 0.002 M β-glycerophosphoric acid disodium salt pentahydrate (β-GP) electrolyte may be used.

In this case, among the Ca and P ions incorporated in the oxide layer by the microarc oxidation (MAO) treatment, Ca ions may be dissolved out rapidly, which may react with the P ions present in the hydrothermal treatment solution to form the bone component hydroxyapatite ($Ca_5(PO_4)_3(OH)$) on the implant surface, to increase the osteoconductivity of the implant.

According to one embodiment of the present disclosure, the hydrothermal treatment may be performed at a temperature of about 150° C. to 200° C. for 3 hours to 5 hours. As the temperature for hydrothermal treatment increases, the time for hydrothermal treatment becomes shorter. When the hydrothermal treatment is performed within the above-described temperature range, desirable sized crystallites including hydroxyapatite and titanium oxide may be formed within an appropriate treatment time. Thus, the hydrothermal treatment is preferably performed within the above-described temperature range and time range. More preferably, the hydrothermal treatment is performed at a temperature of about 175° C. to 185° C. for about 4 hours.

According to another aspect of the present disclosure, a titanium implant whose surface has a roughness of 2 to 3.5 μm with hybrid structure formed by the method according to the above-described method is provided, wherein the hybrid structure has microstructures on which nano-structured titanium oxide layer is formed.

A titanium implant according to one embodiment of the present disclosure has microstructures formed by anodic oxidation and nanocrystalline structures formed by microarc oxidation and hydrothermal treatment, and has a surface roughness within the above-described range, so that it may have a high bond strength between implant and bone.

The roughness within the above-described numerical range may be obtained by performing observation at 10× magnification using a non-contact three-dimensional microscopic analyzer (3D optical profiler, NV-E1000, Nanosystem, Korea) and calculating an arithmetical average roughness (Ra).

Hereinafter, the present disclosure will be described in detail with reference to examples. However, the examples according to the present disclosure may be modified into various different forms, and the scope of the present disclosure is not interpreted as being limited to the examples described below. The examples of the present specification are provided to more completely explain the present disclosure to those skilled in the art.

Example 1 (Ti-ANO-MAO-HT)

Surface Treatment of Titanium Specimen

Commercially pure titanium (CP-Ti; ASTM Grade 2, Daito Steel Co. Ltd., Japan) was prepared as a disk-shaped specimen having a diameter of 20 mm and a thickness of 1 mm. The specimen surface was polished with SiC polishing paper sequentially from #240 to #2000, and then ultrasonically cleansed with each of acetone, ethanol and distilled water for 5 minutes. The specimen was cleaned again with ethanol, and then finally cleaned with triple distilled water and dried. The prepared specimen was immersed as an anode in 0.2 M $CaCl_2$ aqueous solution, and a platinum wire was connected as a cathode to an anodic oxidation treatment device. Anodic oxidation was performed for 100 cycles, each consisting of application of a pulse with a current density of 0.64 $A/cm^2$ for 1 second and rest for 4 seconds. After the anodic oxidation, the titanium specimen having a titanium oxide layer formed thereon was cleansed ultrasonically with distilled water for 1 hour, and then acid-etched by being immersed in 2% hydrofluoric acid solution (JT Baker) for 15 to 20 seconds, to remove the oxide layer formed on the titanium specimen. After the acid treatment, the specimen was ultrasonically treated with distilled water. The prepared specimen was treated by microarc oxidation through the following process. As an electrolyte for microarc oxidation treatment, a solution containing 0.2 M calcium acetate monohydrate (CA) and 0.02 M β-glycerophosphoric acid disodium salt pentahydrate (β-GP) was used. The titanium specimen was immersed as an anode in this electrolyte, and a platinum wire was used as a cathode. The titanium specimen was subjected to microarc oxidation treatment by applying a constant current of 25.5 $mA/cm^2$ for 180 seconds, to form a titanium oxide layer again on the surface of the titanium specimen. The treated specimen was immersed in a 0.002M β-GP-containing alkaline solution prepared by adding NaOH to distilled water and adjusting the pH to 11, and was then hydrothermally treated at a temperature of 180° C. for 4 hours.

Example 2 (TI-ANO-MAO)

A titanium implant specimen was obtained by treating a specimen in the same manner as Example 1, except that the specimen was not hydrothermally treated.

Comparative Example 1 (TI-MAO)

The same CP-Ti disk specimen used in Example 1 was polished, cleansed and dried, followed by microarc oxidation treatment in an electrolyte containing 0.2 M CA and 0.02 M β-GP. The titanium specimen was immersed as an anode, and a platinum wire was used as a cathode. A constant current of 25.5 $mA/cm^2$ was applied for 180 seconds, to obtain a titanium implant specimen.

Reference Example 1 (CP-Ti)

The same CP-Ti disk specimen used in Example 1 was simply polished, cleansed and dried without surface treatment.

Reference Example 2 (Ti-ANO)

A titanium implant specimen was prepared by treating a specimen in the same manner as Example 1, except that the specimen was not applied with microarc oxidation and hydrothermally treatments.

Measurement of Surface Roughness

The surface roughnesses of the specimens were measured by observing the three-dimensional surface images of the titanium metal specimens of Example 1, Example 2, Comparative Example 1 and Reference Example 2 using a non-contact three-dimensional microscopic analyzer (3D optical profiler, NV-E1000, Nanosystem, Korea) and calculating the arithmetical average roughness (Ra) of each specimen from the surface images.

X-Ray Diffraction Analysis

Using an X-ray diffractometer (XRD; PANalytical, X'Pert PRO, Netherlands), the X-ray diffraction (XRD) patterns of the titanium metal specimens of Examples 1 and 2 and the non-surface-treated titanium specimen of Reference Example 1 were analyzed.

Measurement of Contact Angle

In order to evaluate the hydrophilicities of the titanium metal specimens of Examples 1 and 2 and the non-surface-treated titanium specimen of Reference Example 1, the contact angle of each specimen was measured by a sessile drop method using distilled water. A droplet was placed on the surface of each specimen, and after 5 seconds, the shape of the droplet was saved as an image, and then the contact angle was calculated from the shape of the droplet.

Figure 2:
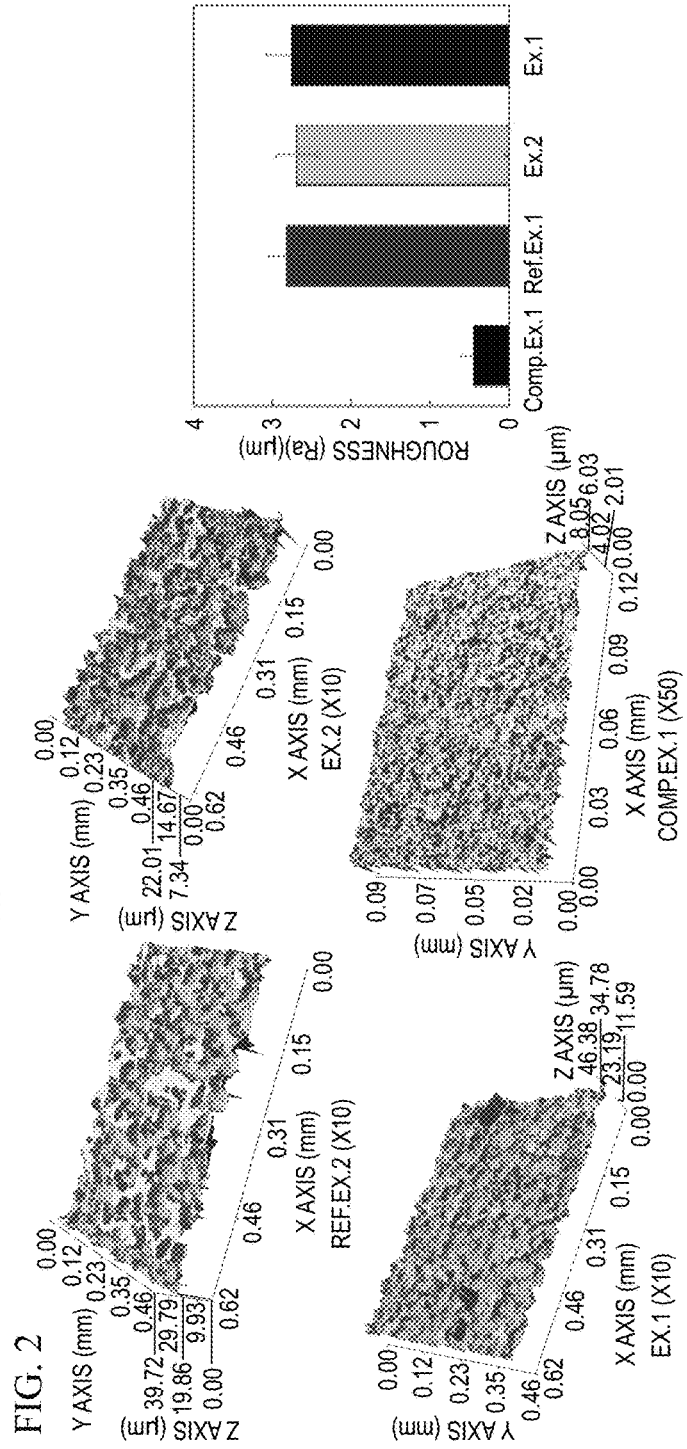
FIG. 2 shows images obtained by observing titanium implant specimens of Example 1, Example 2, Comparative Example 1 and Reference Example 2 using a non-contact three-dimensional microscopic analyzer (3D optical profiler, NV-E1000, Nanosystem, Korea), and the results obtained by calculating the arithmetical average roughness (Ra) from these images.
Figure 3:
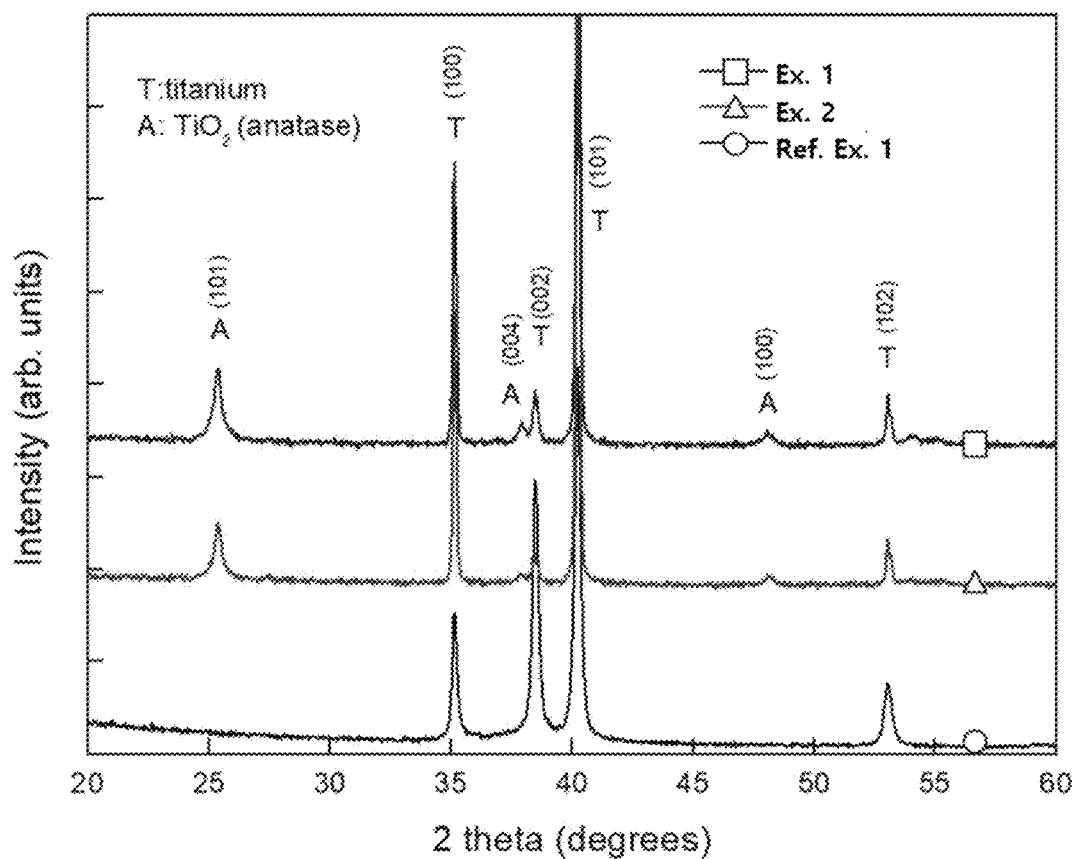
FIG. 3 shows the results of X-ray diffraction (XRD) analysis for titanium specimens of Examples 1 and 2 and a non-surface-treated titanium specimen of Reference Example 1.
Figure 4:
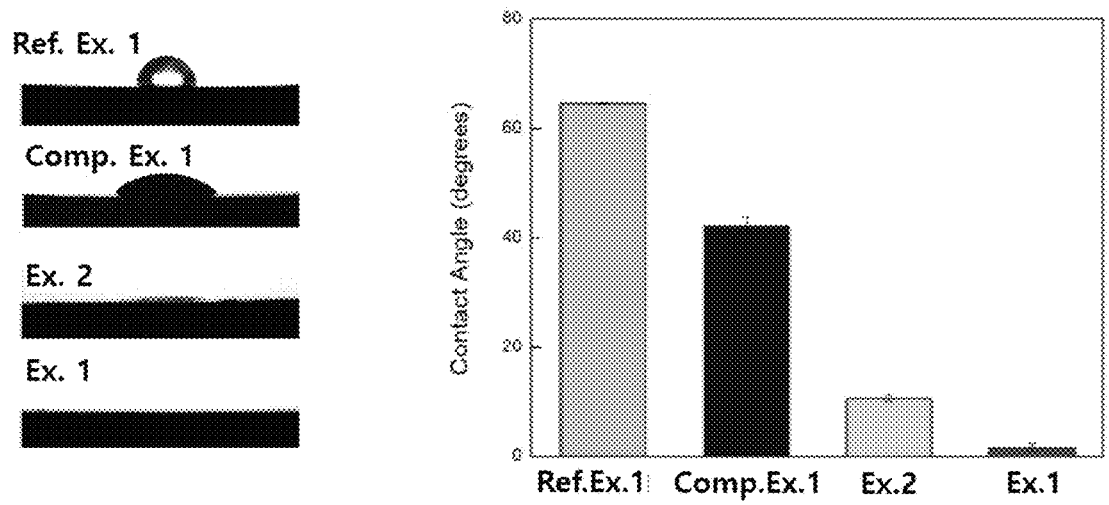
FIG. 4 shows the results of measuring the contact angles for titanium specimens of Examples 1 and 2 and Comparative Example 1 and a non-surface-treated titanium specimen of Reference Example 1.

The results of the respective measurements are shown in FIGS. 2 to 4.

FIG. 2 shows the results of measuring the three-dimensional surface images and roughnesses of the titanium metal specimens of Examples 1 and 2, Comparative Example 1 and Reference Example 2. As can be seen therein, although Comparative Example 1 was imaged at a higher magnification (50×) than other surface images (10×), it showed a less rough surface shape than Examples 1 and 2 and Reference Example 2. In addition, from the results of measurement of the roughnesses, it can be seen that Reference Example 2 had a roughness of about 2.8 μm which was higher than the roughness of Comparative Example 1 (0.45 μm), and that the roughness was maintained even in Examples 1 and 2 in which the titanium specimen of Reference Example 2 was additionally surface-modified. Thus, the treatment method of the present disclosure can compensate for a low roughness value which is the disadvantage of a conventional method (Comparative Example 1) of imparting high roughness to the surface of a titanium implant material only by microarc oxidation treatment.

FIG. 3 shows the results of X-ray diffraction (XRD) analysis of the titanium metal specimens of Examples 1 and 2 and the surface-non-treated titanium specimen of Reference Example 1. As can be seen therein, an A (100) peak and A (101) peak corresponding to anatase titanium dioxide peaks were observed in Examples 1 and 2. This indicates that a titanium oxide layer was formed by microarc oxidation after anodic oxidation. In particular, it is considered that the reason why the intensity of the titanium dioxide peaks in Example 1 was greater than the intensity of the peaks in Example 2 was because the titanium dioxide was further crystallized by hydrothermal treatment.

FIG. 4 shows the results of measuring the contact angles of the titanium metal specimens of Examples 1 and 2 and Comparative Example 1 and the surface-non-treated titanium specimen of Reference Example 1. Generally, the lower the contact angle is, the higher the hydrophilicity is. Reference Example 1 showed a high contact angle of about 60°. The surface of the titanium specimen of Comparative Example 1 showed a contact angle of about 40°, which is slightly lower than that of the titanium specimen of Reference Example 1. It can be seen that the specimen of Example 2 showed a contact angle of about 10°, and thus was hydrophilic. In particular, it can be confirmed that Example 1 showed a contact angle lower than 2°, and thus was very high hydrophilic. Therefore, the treatment method of the present disclosure may increase the bone bonding strength of the titanium implant by increasing the surface hydrophilicity of the titanium implant, compared to the method of performing only microarc oxidation treatment.

Taking the above-described results together, it can be seen that the physical properties of the titanium implant according to one embodiment of the present disclosure are better than the physical properties of the conventional titanium implant.

As described above, the method for surface treatment of a titanium implant material according to one embodiment of the present disclosure may provide a titanium implant having higher bond strength between implant and bone by imparting higher roughness and hydrophilicity.

The effects of the present disclosure are not limited to the above-described effect, and effects which are not mentioned will be clearly understood by those skilled in the art from the present specification and the accompanying drawings.

While various embodiments have been described above, it will be understood to those skilled in the art that the embodiments described are by way of example only. Accordingly, the disclosure described herein should not be limited based on the described embodiments.

What is claimed is:

1. A method for surface treatment of a titanium implant material, the method comprising:
    anodically oxidizing the titanium implant material in a chloride electrolyte solution by application of electrical pulses, to form a microstructured-surface of the titanium implant material and a titanium oxide layer on the titanium implant material at the same time;
    acid-etching the titanium implant material having the microstructured-surface and the titanium oxide layer thereon, to remove the titanium oxide layer on the titanium implant material; and
    performing microarc oxidation on the titanium implant material from which the titanium oxide layer has been removed, to form a titanium oxide layer again on the microstructured-surface of the titanium implant material,
    wherein the chloride electrolyte solution contains one or more of $CaCl_2$, NaCl and simulated body fluid (SBF),
    wherein the electrical pulses are applied with a current density of 0.5 $A/cm^2$ to 3 $A/cm^2$ to the titanium implant material, and
    wherein the titanium implant material is connected as an anode when anodically oxidizing the titanium implant material in the chloride electrolyte solution.

2. The method of claim 1, wherein the chloride electrolyte solution has a chlorine ion concentration of 0.2 M to 1.0 M.

3. The method of claim 1, wherein the acid-etching is performed using hydrofluoric acid.

4. The method of claim 1, further comprising, after the step of forming the titanium oxide layer again on the microstructured-surface of the titanium implant material, a step of hydrothermally treating the titanium implant material.

5. The method of claim 4, wherein the step of hydrothermally treating is performed at a temperature of 150° C. to 200° C. for 3 hours to 5 hours.

6. A titanium implant material whose surface has a roughness of 2 to 3.5 μm with a hybrid structure, wherein the hybrid structure has microstructures on which a nanostructured titanium oxide layer is formed, and
    wherein the surface of the titanium implant material is treated by:
    anodically oxidizing the titanium implant material in a chloride electrolyte solution by application of electrical pulses, to form a microstructured-surface of the titanium implant material and a titanium oxide layer on the titanium implant material at the same time;
    acid-etching the titanium implant material having the microstructured-surface and the titanium oxide layer thereon, to remove the titanium oxide layer on the titanium implant material; and
    performing microarc oxidation on the titanium implant material from which the titanium oxide layer has been removed, to form a titanium oxide layer again on the microstructured-surface of the titanium implant material,
    wherein the chloride electrolyte solution contains one or more of $CaCl_2$, NaCl and simulated body fluid (SBF),
    wherein the electrical pulses are applied with a current density of 0.5 $A/cm^2$ to 3 $A/cm^2$ to the titanium implant material, and
    wherein the titanium implant material is connected as an anode when anodically oxidizing the titanium implant material in the chloride electrolyte solution.

* * * * *